United States Patent
Sato et al.

(10) Patent No.: US 12,036,526 B2
(45) Date of Patent: Jul. 16, 2024

(54) CARBON DIOXIDE REDUCTION DEVICE

(71) Applicant: Nippon Telegraph and Telephone Corporation, Tokyo (JP)

(72) Inventors: Sayumi Sato, Musashino (JP); Yuya Uzumaki, Musashino (JP); Yoko Ono, Musashino (JP); Takeshi Komatsu, Musashino (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 784 days.

(21) Appl. No.: 17/057,532

(22) PCT Filed: May 17, 2019

(86) PCT No.: PCT/JP2019/019633
§ 371 (c)(1),
(2) Date: Nov. 20, 2020

(87) PCT Pub. No.: WO2019/225494
PCT Pub. Date: Nov. 28, 2019

(65) Prior Publication Data
US 2021/0197166 A1 Jul. 1, 2021

(30) Foreign Application Priority Data
May 22, 2018 (JP) ................................. 2018-098089

(51) Int. Cl.
*B01J 19/12* (2006.01)
*C01B 32/40* (2017.01)
(Continued)

(52) U.S. Cl.
CPC ............ *B01J 19/122* (2013.01); *C01B 32/40* (2017.08); *C07C 1/12* (2013.01); *C25B 3/26* (2021.01);
(Continued)

(58) Field of Classification Search
CPC ... B01J 19/00; B01J 19/08; B01J 19/12; B01J 19/122; B01J 2219/00; B01J 2219/08;
(Continued)

(56) References Cited

U.S. PATENT DOCUMENTS

| | | | | |
|---|---|---|---|---|
| 9,339,764 | B2 * | 5/2016 | Lin | .................. B01D 61/48 |
| 9,551,077 | B2 * | 1/2017 | Deguchi | .................. C25B 3/25 |
| 2014/0360883 | A1 | 12/2014 | Deguchi et al. | |
| 2016/0369409 | A1 | 12/2016 | Kudo et al. | |
| 2017/0247804 | A1 | 8/2017 | Yamada et al. | |

FOREIGN PATENT DOCUMENTS

| | | |
|---|---|---|
| JP | 2017-155336 A | 9/2017 |
| WO | 2014/034004 A1 | 3/2014 |
| WO | 2015/146014 A1 | 10/2015 |

OTHER PUBLICATIONS

International Search Report dated Jul. 16, 2019, issued in PCT Application No. PCT/JP2019/019633, filed May 17, 2019.
(Continued)

*Primary Examiner* — Natasha E Young
(74) *Attorney, Agent, or Firm* — Workman Nydegger

(57) ABSTRACT

Improvement in the efficiency of carbon dioxide reduction reaction is achieved. A gas supply unit having a plurality of pores is established in a lower portion of a reduction chamber, and carbon dioxide is supplied as bubbles into an aqueous solution. This can elevate a concentration of carbon dioxide dissolved in the aqueous solution without stirring the aqueous solution using a stirring bar, and render the concentration uniform in the aqueous solution. Therefore, the efficiency of reduction reaction of carbon dioxide in a reduction electrode can be improved.

4 Claims, 3 Drawing Sheets

(51) Int. Cl.
  *C07C 1/12* (2006.01)
  *C25B 3/26* (2021.01)
  *C25B 9/19* (2021.01)
  *C25B 9/50* (2021.01)

(52) U.S. Cl.
  CPC .............. *C25B 9/19* (2021.01); *C25B 9/50* (2021.01); *B01J 2219/0877* (2013.01); *B01J 2219/1203* (2013.01)

(58) Field of Classification Search
  CPC ........ B01J 2219/0873; B01J 2219/0877; B01J 2219/12; B01J 2219/1203; C07C 1/00; C07C 1/02; C07C 1/12; C25B 1/00; C25B 1/01; C25B 1/02; C25B 1/04; C25B 1/2355; C25B 3/00; C25B 3/01; C25B 3/20; C25B 3/2526; C25B 9/00; C25B 9/17; C25B 9/19; C25B 9/50
  See application file for complete search history.

(56) References Cited

OTHER PUBLICATIONS

Yoshi Hori et al., *Formation of Hydrocarbons in the Electrochemical Reduction of Carbon Dioxide at a Copper Electrode in Aqueous Solution*, Journal of Chem. Soc. Faraday, Trans., vol. 85, No. 8, 1989, pp. 2309-2326.

Heng Zhong et al., *Effect of $KHCO_3$ Concentration of Electrochemical Reduction of $CO_2$ on Copper Electrode*, Journal of the Electrochemical Society, vol. 164, No. 9, 2017, pp. F923-F927.

S. Yotsuhashi, et al., *$CO_2$ Conversion with Light and Water by GaN Photoelectrode*, Japanese Journal of Applied Physics, vol. 51, No. 2S, 2012, pp. 1-4.

Hiroshi Hashiba et al., *Selectivity Control of $CO_2$ Reduction in an Inorganic Artificial Photosynthesis System*, Applied Physics Express, vol. 6, No. 9, 2013, pp. 1-5.

* cited by examiner

CARBON DIOXIDE REDUCTION DEVICE

CROSS REFERENCE TO RELATED APPLICATIONS

The present application is a 35 U.S.C. § 371 National Phase conversion of International (PCT) Patent Application No. PCT/JP2019/019633, filed on May 17, 2019, which claims priority of Japanese Patent Application No. 2018-098089, filed on May 22, 2018, the disclosure of which is incorporated by reference herein.

TECHNICAL FIELD

The present invention relates to a technique of reducing carbon dioxide with electric or light energy.

BACKGROUND ART

Conventional carbon dioxide reduction devices are configured such that: an oxidation chamber where an oxidation electrode is dipped in an aqueous solution and a reduction chamber where a reduction electrode is dipped in an aqueous solution are connected via a proton exchange membrane; and carbon dioxide is constantly supplied to the reduction chamber from a tube. A power source is connected to between the electrodes so that electric energy is supplied thereto. Alternatively, the electrodes are electrically connected with each other, and light energy is supplied to the oxidation electrode through light irradiation. As a result, a reaction proceeds in each electrode. A proton produced by the oxidation reaction of water in the oxidation electrode is transported to the reduction chamber via the proton exchange membrane. In the reduction electrode, hydrogen is produced by the reduction reaction of the proton, and carbon monoxide, methane, ethylene, methanol, ethanol, and formic acid, etc. are produced by the reduction reaction of carbon dioxide.

CITATION LIST

Non-Patent Literature

Non-Patent Literature 1: Y. Hori, et al., "Formation of Hydrocarbons in the Electrochemical Reduction of Carbon Dioxide at a Copper Electrode in Aqueous Solution", Journal of the Chemical Society, 1989, 85 (8), 2309-2326

Non-Patent Literature 2: H. Zhong, et al., "Effect of KHCO3 Concentration on Electrochemical Reduction of CO2 on Copper Electrode", Journal of The Electrochemical Society, 2017, 164 (9), F923-F927

Non-Patent Literature 3: S. Yotsuhashi, et al., "CO2 Conversion with Light and Water by GaN Photoelectrode", Japanese Journal of Applied Physics 51, 2012, 02BP07

Non-Patent Literature 4: H. Hashiba, et al., "Selectivity Control of CO2 Reduction in an Inorganic Artificial Photosynthesis System", Applied Physics Express 6, 2013, 097102

SUMMARY OF THE INVENTION

Technical Problem

For improving the efficiency of reduction reaction of carbon dioxide, it is necessary to uniformly supply a high concentration of carbon dioxide to the surface of a reduction electrode. Unfortunately, conventional supply using a tube has the difficulty in uniformly contacting carbon dioxide with the reduction electrode. It is possible to uniformly disperse bubbles of carbon dioxide by stirring a solution in the reduction chamber using a stirring bar or the like. However, a problem of this approach is the consumption of electric to drive the stirring bar, increasing cost and environmental load.

The present invention has been made in light of these circumstances, and an object of the present invention is to achieve improvement in the efficiency of carbon dioxide reduction reaction.

Means for Solving the Problem

The carbon dioxide reduction device according to the present invention is a carbon dioxide reduction device which causes reduction reaction in a reduction electrode by applying current to between an oxidation electrode and the reduction electrode, the carbon dioxide reduction device comprising: an oxidation chamber for dipping and disposing the oxidation electrode in an aqueous solution; a reduction chamber for dipping and disposing the reduction electrode in an aqueous solution; a proton exchange membrane disposed between the oxidation chamber and the reduction chamber; and a carbon dioxide supply unit disposed in a lower portion of the reduction chamber and having a plurality of pores for supplying carbon dioxide as bubbles into the aqueous solution.

Effects of the Invention

The present invention can achieve improvement in the efficiency of carbon dioxide reduction reaction.

DESCRIPTION OF EMBODIMENTS

Hereinafter, the embodiments of the present invention will be described with reference to the drawings. The present invention is not limited by Examples given below, and changes or modifications may be added to the present invention without departing from the spirit of the present invention.

First Embodiment

Figure 1:
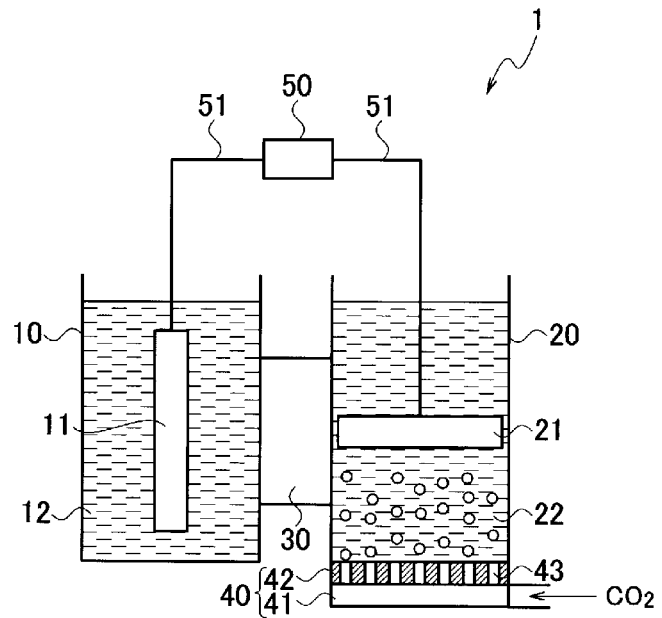
FIG. 1 is a schematic configuration diagram showing the configuration of the carbon dioxide reduction device of a first embodiment.

FIG. 1 is a schematic configuration diagram showing the configuration of the carbon dioxide reduction device of a first embodiment.

A carbon dioxide reduction device 1 of the present embodiment comprises: an oxidation chamber 10; a reduction chamber 20; a proton exchange membrane 30 which permits proton transfer between the oxidation chamber 10 and the reduction chamber 20; a gas supply unit 40 disposed at the bottom of the reduction chamber 20, the gas supply unit 40 supplying carbon dioxide; and a power source 50 which applies current to between an oxidation electrode 11 and a reduction electrode 21.

An aqueous solution 12 is placed in the oxidation chamber 10, and the oxidation electrode 11 is dipped in the aqueous solution 12. The oxidation electrode 11 is electrically connected to the power source 50 through a conductor wire 51. For example, platinum, gold, silver, copper, indium, or nickel can be used in the oxidation electrode 11. For example, an aqueous sodium hydroxide solution, an aqueous potassium chloride solution, or an aqueous sodium chloride solution can be used in the aqueous solution 12.

An aqueous solution 22 is placed in the reduction chamber 20, and the reduction electrode 21 is dipped in the aqueous solution 22. The reduction electrode 21 is electrically connected to the power source 50 through the conductor wire 51. The reduction electrode 21 is made of a metal in the form of a plate, and, for example, copper, gold, platinum, silver, palladium, gallium, indium, nickel, tin, or cadmium can be used. The reduction electrode 21 is disposed such that a reaction surface faces the gas supply unit 40. The reduction electrode 21 may be a wire mesh, or an electrode substrate composed of an electroconductive substrate coated with metal particles in the form of particles. For example, an aqueous potassium bicarbonate solution, an aqueous potassium chloride solution, or an aqueous sodium hydroxide solution can be used in the aqueous solution 22.

For example, Nafion® can be used in the proton exchange membrane 30. Nafion is a perfluorocarbon material constituted by a hydrophobic Teflon backbone consisting of carbon-fluorine, and a perfluoro side chain having a sulfonic acid group.

Figure 2:
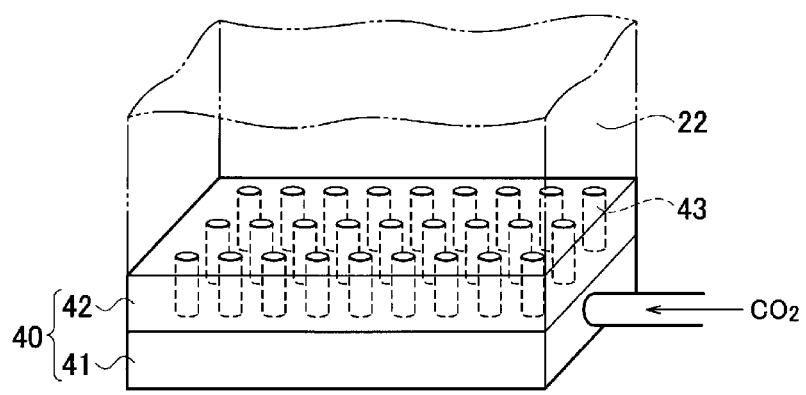
FIG. 2 is a perspective view showing the configuration of a gas supply unit.

The gas supply unit 40 planarly supplies bubbles of carbon dioxide from the bottom of the reduction chamber 20. As shown in FIG. 2, the gas supply unit 40 is constituted by a gas introduction unit 41 and a bubble production unit 42. The gas introduction unit 41 is hollow, and a gas can be sent thereinto from piping. The bubble production unit 42 is a rectangular plate having a large number of tubular pores 43, and is disposed as the upper surface of the gas introduction unit 41. A coverage rate, which is the ratio of the pores 43 to the lower surface of the reduction chamber 20, is 20%. The pores 43 may be formed so as to attain a coverage rate of 10% to 90%. The diameter of the pores 43 can be arbitrarily set to approximately 0.5 mm to approximately 5.0 mm.

When a gas is sent into the gas introduction unit 41, the gas is passed through the pores 43 of the bubble production unit 42 and released as bubbles into the aqueous solution 22. The carbon dioxide reduction device 1 of the present embodiment comprising the gas supply unit 40 which planarly supplies fine bubbles of carbon dioxide can elevate a concentration of carbon dioxide dissolved in the aqueous solution 22 and can also render the concentration of carbon dioxide uniform in the aqueous solution 22.

The power source 50 applies current to between the oxidation electrode 11 and the reduction electrode 21 by the application of voltage.

Upon application of voltage, oxygen is produced by the oxidation reaction of water ($2H_2O \rightarrow O_2 + 4H^+ + 4e^-$) in the oxidation chamber 10. In the reduction chamber 20, hydrogen is produced by the reduction reaction of a proton ($2H^+ + 2e^- \rightarrow H_2$) while carbon monoxide, methane, ethylene, and the like are produced by the reduction reaction of carbon dioxide.

For example, hydrogen production by proton reduction and ammonia production by nitrogen reduction reaction are also possible by changing carbon dioxide to be supplied to the reduction chamber 20 to another gas.

Second Embodiment

Figure 3:
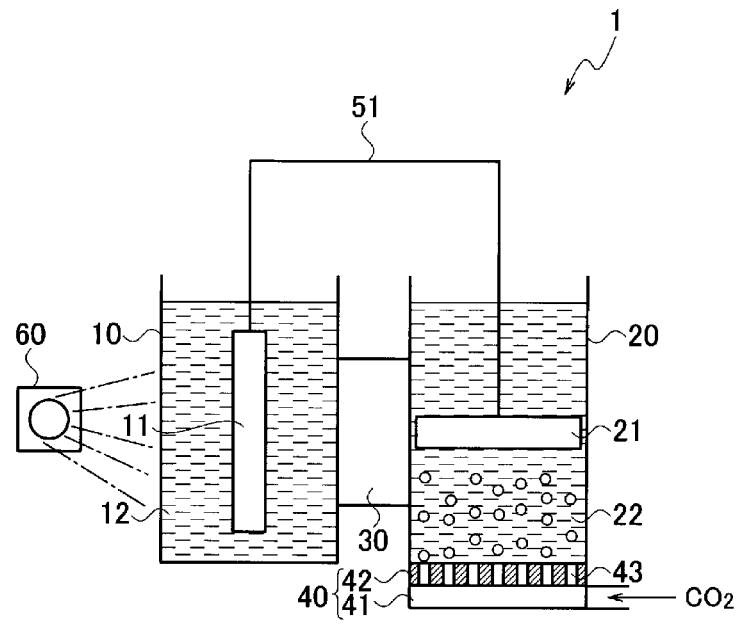
FIG. 3 is a schematic configuration diagram showing the configuration of the carbon dioxide reduction device of a second embodiment.

FIG. 3 is a schematic configuration diagram showing the configuration of the carbon dioxide reduction device of a second embodiment.

A carbon dioxide reduction device 1 of the present embodiment comprises: an oxidation chamber 10; a reduction chamber 20; a proton exchange membrane 30 which permits proton transfer between the oxidation chamber 10 and the reduction chamber 20; a gas supply unit 40 disposed at the bottom of the reduction chamber 20, the gas supply unit 40 supplying carbon dioxide; and a light source 60. The carbon dioxide reduction device 1 of the second embodiment differs from that of the first embodiment in that: a photocatalyst that causes chemical reaction through light irradiation is used in an oxidation electrode 11; and the light source 60 is used instead of the power source 50.

An aqueous solution 12 is placed in the oxidation chamber 10, and the oxidation electrode 11 is dipped in the aqueous solution 12. For example, a compound exhibiting optical activity or redox activity, such as a nitride semiconductor, titanium oxide, amorphous silicon, a ruthenium complex, or a rhenium complex can be used in the oxidation electrode 11. For example, an aqueous sodium hydroxide solution, an aqueous potassium chloride solution, or an aqueous sodium chloride solution can be used in the aqueous solution 12.

An aqueous solution 22 is placed in the reduction chamber 20, and the reduction electrode 21 is dipped in the aqueous solution 22. The oxidation electrode 11 and the reduction electrode 21 are electrically connected through a conductor wire 51. The reduction electrode 21 is in the form of a plate, and, for example, copper, gold, platinum, indium, tungsten(VI) oxide, copper(II) oxide, or a porous metal complex having a metal ion and an anionic ligand can be used. The reduction electrode 21 is disposed such that a wide surface faces the gas supply unit 40. The reduction electrode 21 may be a wire mesh, or an electrode substrate composed of an electroconductive substrate coated with metal particles in the form of particles. For example, an aqueous potassium bicarbonate solution, an aqueous potassium chloride solution, or an aqueous sodium hydroxide solution can be used in the aqueous solution 22.

Nafion® can be used in the proton exchange membrane 30, as in the first embodiment.

The same gas supply unit 40 as that of the first embodiment is used.

The light source 60 is disposed to face a reaction surface of the oxidation electrode 11, and irradiates the oxidation electrode 11 with light. For example, a xenon lamp, a solar simulator, a halogen lamp, a mercury lamp, or sunlight can be used in the light source 60. These light sources 60 may be used in combination.

When the oxidation electrode 11 is irradiated with light, current is applied to between the oxidation electrode 11 and the reduction electrode 21. Oxygen is produced by the oxidation reaction of water in the oxidation chamber 10. In the reduction chamber 20, hydrogen is produced by the reduction reaction of a proton while carbon monoxide, methane, ethylene, and the like are produced by the reduction reaction of carbon dioxide.

Examples and Evaluation Results

Next, the carbon dioxide reduction device 1 of each of the first and second embodiments will be described with reference to Examples using varying diameters of the pores 43 of the gas supply unit 40, and Comparative Examples employing carbon dioxide supply using a tube. First, the first embodiment will be described as to Examples 1 to 4 using varying diameters of the pores 43, and Comparative Example 1 employing carbon dioxide supply using a tube.

Example 1

In Example 1, the diameter of the pores 43 of the gas supply unit 40 in the carbon dioxide reduction device 1 of the first embodiment shown in FIG. 1 was set to 0.5 mm.

Platinum (manufactured by The Nilaco Corporation) was used in the oxidation electrode 11, which was placed in the oxidation chamber 10 such that approximately 0.55 cm 2 of the surface area was immersed in the aqueous solution 12.

The aqueous solution 12 was a 1 mol/l aqueous sodium hydroxide solution.

The reduction electrode 21 used was a copper plate (manufactured by The Nilaco Corporation) cut into 2 cm×3 cm, surface-washed with pure water, and dried. The reduction electrode 21 was placed such that the whole copper plate was immersed in the aqueous solution 22.

The aqueous solution 22 was a 0.5 mol/l aqueous potassium bicarbonate solution.

Nafion® was used in the proton exchange membrane 30.

The diameter of the pores 43 of the bubble production unit 42 was 0.5 mm.

Carbon dioxide was supplied at a flow rate of 20 ml/min and a pressure of 0.18 MPa to the reduction chamber 20.

Helium was supplied to the oxidation chamber 10, and carbon dioxide was supplied to the reduction chamber 20. After thorough purging, a voltage of 2.2 V was applied from the power source 50 to apply current to between the oxidation electrode 11 and the reduction electrode 21.

At an arbitrary time during the voltage application, gases were collected from the oxidation chamber 10 and the reduction chamber 20, and reaction products were analyzed in a gas chromatograph. It was confirmed that oxygen was produced in the oxidation chamber 10. It was confirmed that hydrogen, carbon monoxide, methane, and ethylene were produced in the reduction chamber 20.

Example 2

Example 2 differs from Example 1 in that the diameter of the pores 43 was 1.0 mm. Other factors are the same as those of Example 1.

Example 3

Example 3 differs from Example 1 in that the diameter of the pores 43 was 3.0 mm. Other factors are the same as those of Example 1.

Example 4

Example 4 differs from Example 1 in that the diameter of the pores 43 was 5.0 mm. Other factors are the same as those of Example 1.

Comparative Example 1

Figure 4:
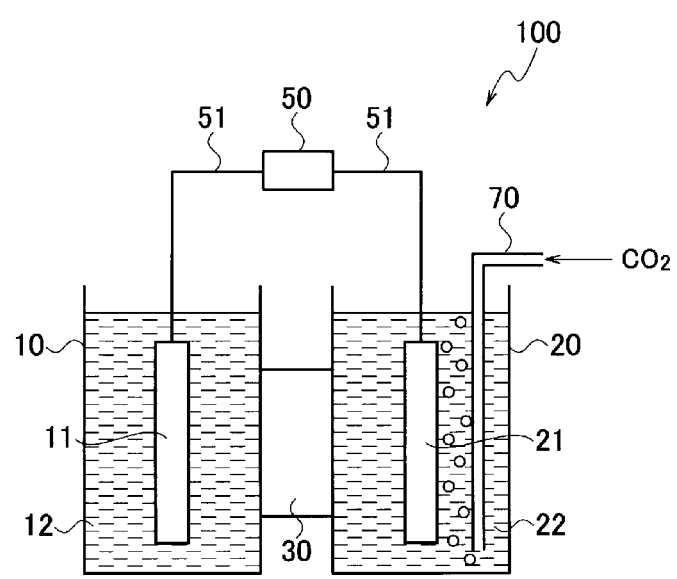
FIG. 4 is a schematic configuration diagram showing the configuration of a carbon dioxide reduction device of Comparative Example 1.

FIG. 4 is a schematic configuration diagram showing the configuration of carbon dioxide reduction device 100 of Comparative Example 1. Comparative Example 1 differs from Examples 1 to 4 in a method for supplying carbon dioxide. The carbon dioxide reduction device 100 of Comparative Example 1 differs from those of Examples 1 to 4 in that: no gas supply unit 40 was included; and carbon dioxide was supplied to near the bottom of a reduction chamber 20 through a tube 70. Other factors are the same as those of Examples 1 to 4.

Evaluation Results of Examples 1 to 4 and Comparative Example 1

As a result of measuring reduction reaction products upon voltage application in Examples 1 to 4, the efficiency of carbon dioxide reduction was improved as compared with Comparative Example 1. Table 1 below shows the Faraday efficiency of each of hydrogen production by proton reduction and substance production by carbon dioxide reduction in Examples 1 to 4 and Comparative Example 1. The Faraday efficiency refers to the ratio of a current value used in reduction reaction to a current value applied to a conductor wire upon voltage application.

TABLE 1

| | $H_2$ production by $H^+$ reduction | Substance production by $CO_2$ reduction |
|---|---|---|
| Example 1 | 39 | 45 |
| Example 2 | 32 | 48 |
| Example 3 | 38 | 42 |
| Example 4 | 47 | 30 |
| Comparative Example 1 | 50 | 24 |

As is evident from Table 1, Examples 1 to 4 compared with Comparative Example 1 improved the Faraday efficiency of substance production by carbon dioxide reduction and reduced the Faraday efficiency of hydrogen production by proton reduction. This shows that the efficiency of reduction reaction of carbon dioxide was improved over that of a proton on the surface of the reduction electrode.

From the results of Examples 1 to 4, no large difference in Faraday efficiency was seen among pore sizes of 3.0 mm or smaller, whereas no large improvement in Faraday efficiency was seen at a pore size of 5.0 mm. This showed that the pore size is preferably 3.0 mm or smaller. This is probably because, when the pore size was 3.0 mm or smaller, a smaller size of bubbles increased the contact area of a gas with the aqueous solution and thus facilitated dissolving carbon dioxide, and in addition, carbon dioxide was able to be uniformly supplied to the reduction electrode.

The Faraday effect is lower in Example 1 (pore size: 0.5 mm) than in Example 2 (pore size: 1.0 mm). This is probably because carbon dioxide less easily passed through the pores so that the amount of carbon dioxide supplied was decreased.

Subsequently, the second embodiment will be described as to Examples 5 to 8 using varying diameters of the pores 43, and Comparative Example 2 employing carbon dioxide supply using a tube.

Example 5

In Example 5, the diameter of the pores 43 of the gas supply unit 40 in the carbon dioxide reduction device 1 of the second embodiment shown in FIG. 3 was set to 0.5 mm.

The oxidation electrode 11 used was a substrate prepared by causing the crystal growth of a thin film of a n-type semiconductor GaN on a sapphire substrate and coating the thin film with NiO as an oxidation promoter thin film. The oxidation electrode 11 was placed in the oxidation chamber 10 such that the oxidation electrode 11 was immersed in the aqueous solution 12.

The aqueous solution 12 was a 1 mol/l aqueous sodium hydroxide solution.

The reduction electrode 21 used was a copper plate (manufactured by The Nilaco Corporation) cut into 2 cm×3 cm, surface-washed with pure water, and dried. The reduction electrode 21 was placed such that the whole copper plate was immersed in the aqueous solution 22.

The aqueous solution 22 was a 0.5 mol/l aqueous potassium bicarbonate solution.

Nafion® was used in the proton exchange membrane 30.

The light source 60 used was a 300 W high-pressure xenon lamp (which cuts off wavelengths of 450 nm or more, illuminance: 2.2 mW/cm 2), and was fixed so as to irradiate a surface having the formed oxidation promoter of the semiconductor light electrode of the oxidation electrode 11. The light irradiation area of the oxidation electrode was set to 1.0 cm 2.

The diameter of the pores 43 of the bubble production unit 42 was 0.5 mm.

Carbon dioxide was supplied at a flow rate of 20 ml/min and a pressure of 0.18 MPa to the reduction chamber 20.

The oxidation chamber 10 and the reduction chamber 20 were thoroughly purged with carbon dioxide and helium. Then, the oxidation electrode 11 was uniformly irradiated with light using the light source 60.

At an arbitrary time during the light irradiation, gases were collected from the oxidation chamber 10 and the reduction chamber 20, and reaction products were analyzed in a gas chromatograph. It was confirmed that oxygen was produced in the oxidation chamber 10. It was confirmed that hydrogen, carbon monoxide, methane, and ethylene were produced in the reduction chamber 20.

Example 6

Example 6 differs from Example 5 in that the diameter of the pores 43 was 1.0 mm. Other factors are the same as those of Example 5.

Example 7

Example 7 differs from Example 5 in that the diameter of the pores 43 was 3.0 mm. Other factors are the same as those of Example 5.

Example 8

Example 8 differs from Example 5 in that the diameter of the pores 43 was 5.0 mm. Other factors are the same as those of Example 5.

Comparative Example 2

Figure 5:
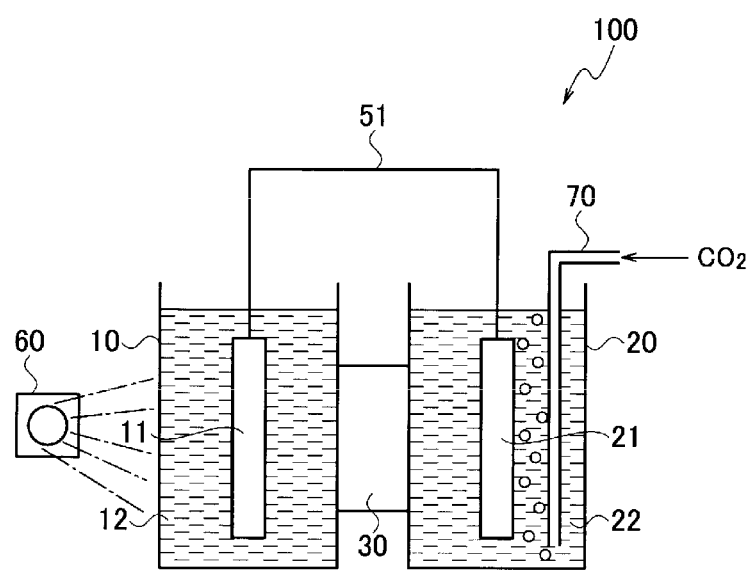
FIG. 5 is a schematic configuration diagram showing the configuration of a carbon dioxide reduction device of Comparative Example 2.

FIG. 5 is a schematic configuration diagram showing the configuration of carbon dioxide reduction device 100 of Comparative Example 2. Comparative Example 2 differs from Examples 5 to 8 in a method for supplying carbon dioxide. The carbon dioxide reduction device 100 of Comparative Example 2 differs from those of Examples 5 to 8 in that: no gas supply unit 40 was included; and carbon dioxide was supplied to near the bottom of a reduction chamber 20 through a tube 70. Other factors are the same as those of Examples 5 to 8.

Evaluation Results of Examples 5 to 8 and Comparative Example 2

As a result of measuring reduction reaction products upon light irradiation in Examples 5 to 8, the efficiency of carbon dioxide reduction was improved as compared with Comparative Example 2. Table 2 below shows the Faraday efficiency of each of hydrogen production by proton reduction and substance production by carbon dioxide reduction in Examples 5 to 8 and Comparative Example 2.

TABLE 2

|  | $H_2$ production by $H^+$ reduction | Substance production by $CO_2$ reduction |
|---|---|---|
| Example 5 | 49 | 23 |
| Example 6 | 42 | 31 |
| Example 7 | 50 | 23 |
| Example 8 | 56 | 18 |
| Comparative Example 2 | 58 | 15 |

As is evident from Table 2, Examples 5 to 8 compared with Comparative Example 2 improved the Faraday efficiency of substance production by carbon dioxide reduction and reduced the Faraday efficiency of hydrogen production by proton reduction. This shows that the efficiency of reduction reaction of carbon dioxide was improved over that of a proton on the surface of the reduction electrode.

The same tendency as that of Examples 1 to 4 was seen as to an effect brought about by difference in pore size.

As described above, according to the present embodiment, a gas supply unit 40 having a plurality of pores 43 is established in a lower portion of a reduction chamber 20, and carbon dioxide is supplied as bubbles into an aqueous solution 22. This can elevate a concentration of carbon dioxide dissolved in the aqueous solution 22 without stirring the aqueous solution 22 using a stirring bar, and render the concentration uniform in the aqueous solution 22. Therefore, the efficiency of reduction reaction of carbon dioxide in a reduction electrode 21 can be improved.

According to the present embodiment, a reduction electrode 21 is disposed such that a reaction surface faces a plurality of pores 43. This can uniformly supply a high concentration of carbon dioxide as bubbles to the whole reaction surface of the reduction electrode 21. As a result, the efficiency of reduction reaction of carbon dioxide in the reduction electrode 21 can be improved.

REFERENCE SIGNS LIST

1 Carbon dioxide reduction device
10 Oxidation chamber
11 Oxidation electrode

12 Aqueous solution
20 Reduction chamber
21 Reduction electrode
22 Aqueous solution
30 Proton exchange membrane
40 Gas supply unit
41 Gas introduction unit
42 Bubble production unit
43 Pore
50 Power source
51 Conductor wire
60 Light source
70 Tube

The invention claimed is:

1. A carbon dioxide reduction device which causes reduction reaction in a reduction electrode by applying current to between an oxidation electrode and the reduction electrode, the carbon dioxide reduction device comprising:
   an oxidation chamber for dipping and disposing the oxidation electrode in an aqueous solution;
   a reduction chamber for dipping and disposing the reduction electrode in an aqueous solution;
   a proton exchange membrane disposed between the oxidation chamber and the reduction chamber; and
   a gas supply unit disposed in a lower portion of the reduction chamber and having a plurality of pores for supplying carbon dioxide as bubbles into the aqueous solution, wherein
   a surface having the plurality of pores of the gas supply unit is disposed to face upward in the reduction chamber; and
   the reduction electrode is disposed such that a reaction surface faces the surface having the plurality of pores.

2. The carbon dioxide reduction device according to claim 1, comprising a power source which applies current to between the oxidation electrode and the reduction electrode.

3. The carbon dioxide reduction device according to claim 1, wherein
   the oxidation electrode causes oxidation reaction by exerting a catalytic function through light irradiation; and
   the carbon dioxide reduction device comprises a light source which irradiates a reaction surface of the oxidation electrode with light.

4. The carbon dioxide reduction device according to claim 2, wherein
   the oxidation electrode causes oxidation reaction by exerting a catalytic function through light irradiation; and
   the carbon dioxide reduction device comprises a light source which irradiates a reaction surface of the oxidation electrode with light.

* * * * *